(12) United States Patent
Hess

(10) Patent No.: US 6,582,422 B2
(45) Date of Patent: Jun. 24, 2003

(54) OPHTHALMIC DELIVERY DEVICE

(75) Inventor: Charles E. Hess, St. Louis, MO (US)

(73) Assignee: Bausch & Lomb Incorporated, Rochester, NY (US)

(*) Notice: Subject to any disclaimer, the term of this patent is extended or adjusted under 35 U.S.C. 154(b) by 0 days.

(21) Appl. No.: 09/970,292

(22) Filed: Oct. 3, 2001

(65) Prior Publication Data

US 2003/0065293 A1 Apr. 3, 2003

(51) Int. Cl.[7] ............................................... A61B 18/18
(52) U.S. Cl. ............................................ 606/4; 128/858
(58) Field of Search .................................. 604/294–301; 128/898, 858; 606/4–6

(56) References Cited

U.S. PATENT DOCUMENTS 5,368,590 A * 11/1994 Itoh ............................ 128/853
5,980,497 A * 11/1999 Yavitz ........................ 128/858

* cited by examiner

Primary Examiner—Weilun Lo
Assistant Examiner—Linh Truong
(74) Attorney, Agent, or Firm—Michael L. Smith

(57) ABSTRACT

Delivery device 10 for use in ophthalmic surgery includes body portion 12 for retaining an agent to be applied to a patient's eye. Body portion 12 includes structure forming a concave surface 14, so that when the delivery device 10 is placed on the eye, the device 10 closely fits to a corneal curvature of the eye.

6 Claims, 1 Drawing Sheet

OPHTHALMIC DELIVERY DEVICE

BACKGROUND OF THE INVENTION

1. Field of the Invention

The present invention is related to devices for delivering an agent to the cornea of an eye and more specifically, to devices delivering an agent to the cornea of the eye where a delivery material retains the agent to be applied to the eye.

2. Description of the Prior Art

A recent development in refractive surgery is laser epithelial keratomileusis (LASEK). This so called LASEK procedure was developed by Dr. Massimo Camellin, and is essentially a modification of photorefractive keratectomy (PRK). In the LASEK procedure, a modified trephine is used to make an incision through the epithelial layer of a patient's cornea. A cylinder is placed on the eye over the epithelial layer outside the trephine cut. Then the cylinder is filled with a loosening agent such as a dehydrated alcohol solution for a given period of time, typically 25–45 seconds. An absorbent material such as a Weck cell or other sponge is then used to absorb the loosening agent. Next, the cornea is typically irrigated with BSS. A sharp instrument is then used to peel back an epithelial flap defined by the trephine cut and which had been treated with the loosening agent. Ablation is then performed on the portion of the cornea where the epithelial layer has been removed in order to correct the patient's vision. The removed epithelial flap is then put back into position over the ablated corneal surface.

The application of the loosening agent to the eye can be a significant source of irritation to the patient, particularly if the loosening agent leaks from the seal between the cylinder and the cornea, thus causing a burning sensation for the patient. Therefore, it would be desirable to provide a device which would significantly reduce the chance for the loosening agent to leak beyond the surgical site.

It is known in the prior art to use a dampened sponge material on the eye for blocking the surgical light from entering the eye during suturing of the wounds. This allows the cornea to stay hydrated. In addition, it is also known to use collagen shields to apply medication, typically steroids or antibiotics immediately following cataract or corneal transplant surgery. However, these corneal collagen shields are used after surgery and are not removed by the doctor, but rather dissolve in the eye naturally over a period of time.

Figure 1:
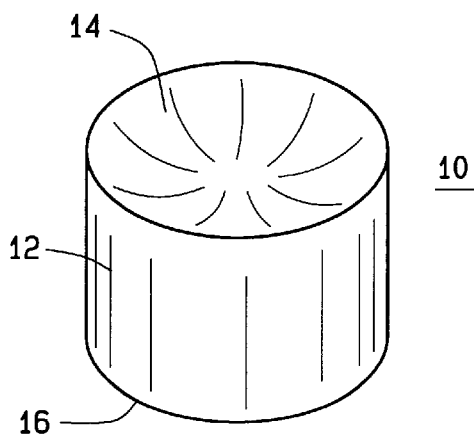
FIG. 1 shows a delivery device in accordance with the present invention.

A delivery device 10 for use in ophthalmic surgery is shown in FIG. 1. Delivery device 10 includes a body portion 12, an eye contact surface 14, and an opposing top surface 16. Body portion 12 is preferably a cylindrical in shape, though not necessarily so, and is formed of a delivery material for retaining an agent (not shown) to be applied to a patient's eye. Body portion 12 preferably includes structure forming concave surface 14, such that when the delivery device 10 is placed on the eye, the device 10 closely fits to a corneal curvature of the eye. This allows the agent to contact the eye at a location defined by the concave surface and effectively prevents the agent from contacting the eye at an undesired location. The delivery material of body portion 12 is preferably a surgical sponge material or other cellular material, but may be any material capable of retaining the agent by surface tension or other non-covalent means that allows the agent to be applied to the eye, and particularly the epithelial layer, upon contact with the concave surface 14.

The agent to be retained by delivery device 10 is preferably a loosening agent, such as the alcohol solution described above for use in LASEK surgery, but may be other agents to be applied to the eye. In practice, the agent may be inserted into the device 10 at the surgery site by the surgical staff, or the agent may be inserted by the manufacturer and delivered to the surgical facility with the agent already retained within the device 10.

Figure 2:
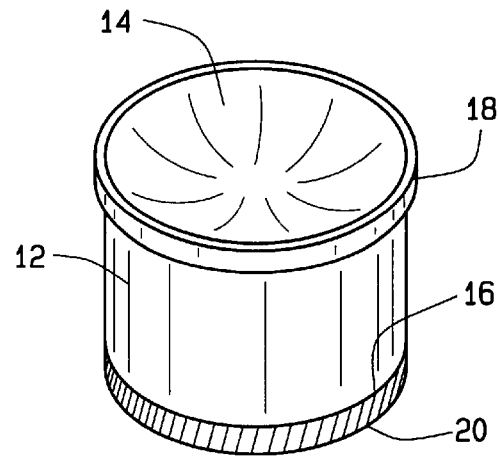
FIG. 2 shows an alternate embodiment of a delivery device in accordance with the present invention.

FIG. 2 discloses an alternative embodiment in accordance with the present invention and is similar to the embodiment of FIG. 1, in that it includes body 12, concave surface 14, and top surface 16 but in addition, includes a support ring 18 and an evaporation shield 20. Support ring 18 provides extra protection against leakage of the loosening agent away from the surgical site. Support ring 18 therefore, further minimizes the chance of unnecessary discomfort to the patient. Evaporation shield 20 may be applied to top surface 16, and is typically a layer of plastic or other material to help prevent drying out of the agent due to the light and heat from the surgical microscope. Support ring 18 is preferably adjacent and surrounding the concave surface 14 to further prevent the agent from the contacting the eye in an undesired location, as shown in FIG. 2.

Figure 3:
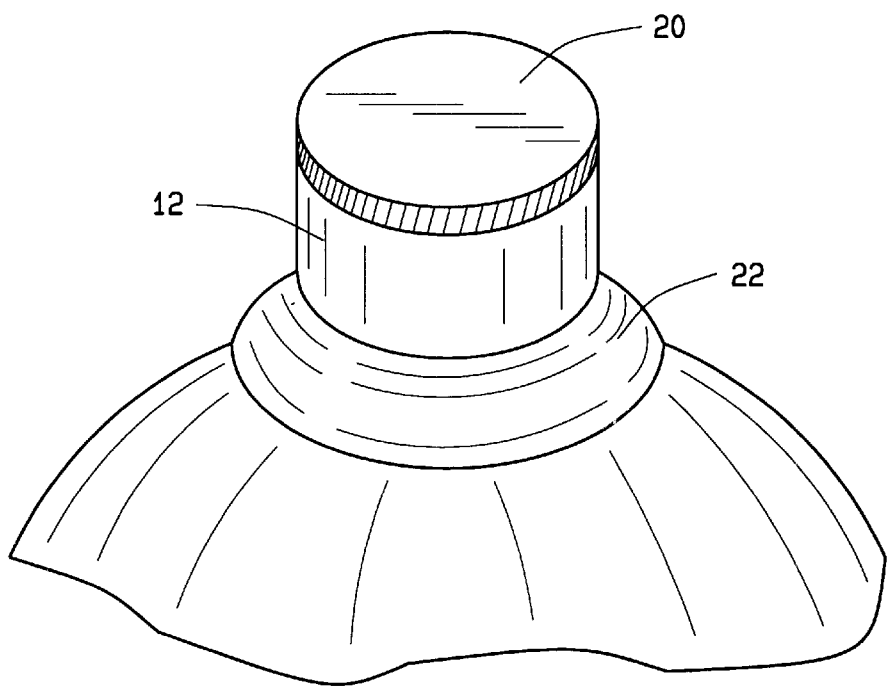
FIG. 3 shows a delivery device in accordance with the present invention applied to a cornea.

FIG. 3 shows a delivery device 10 in accordance with the present invention being applied to a patient's eye 22. As can be seen, the body 12 sits on the cornea with evaporation shield 20 facing any surgical light to minimize any evaporation due to the light or heat from such surgical light source.

Thus, there has been shown a delivery device for retaining and delivering an agent to a patient's eye.

What is claimed is:

1. A delivery device for use in ophthalmic surgery comprising:

a body portion for retaining an agent to be applied to a patient's eye;

wherein the body portion includes structure forming a concave surface such that when the delivery device is placed on the eye the device closely fits to a corneal curvature of the eye thereby allowing the agent to contact the eye at a location defined by the concave surface and effectively preventing the agent from contacting the eye at an undesired location; and a support ring adjacent and surrounding the concave surface for further preventing the agent from contacting the eye at an undesired location.

2. The device of claim 1 further including a shield attached to the body portion at an opposing surface to the concave surface for reducing evaporation of the agent from the device due to surgical light or heat.

3. The device of claim 1 wherein the body portion is a sponge or other material capable of retaining the agent by surface tension or other non-covalent means.

4. The device of claim 1 further including the agent to be applied to the eye wherein the agent is retained by the body portion.

5. An agent application device for use in ophthalmic surgery comprising:

a sponge;

a loosening agent contained within the sponge;

wherein the sponge includes structure forming a concave surface such that when the concave surface is placed on a patient's eye the loosening agent interacts with an epithelial layer of the eye at a location defined by the concave surface; and a support ring adjacent and surrounding the concave surface for assisting in maintaining the agent within a boundary defined by an outer edge of the concave surface.

6. The device of claim 5 further including a shield attached to the sponge at an opposing surface to the concave surface for reducing evaporation of the agent from the device due to surgical light or heat.

* * * * *